(12) United States Patent
Pacetti et al.

(10) Patent No.: US 8,092,822 B2
(45) Date of Patent: Jan. 10, 2012

(54) COATINGS INCLUDING DEXAMETHASONE DERIVATIVES AND ANALOGS AND OLIMUS DRUGS

(75) Inventors: Stephen D. Pacetti, San Jose, CA (US); John L. Toner, Libertyville, IL (US); Keith R. Cromack, Chesterfield, MO (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 20 days.

(21) Appl. No.: 12/240,917

(22) Filed: Sep. 29, 2008

(65) Prior Publication Data

US 2010/0082095 A1   Apr. 1, 2010

(51) Int. Cl.
*A61F 2/00* (2006.01)
(52) U.S. Cl. ............................................ 424/423
(58) Field of Classification Search .................. None
See application file for complete search history.

(56) References Cited

U.S. PATENT DOCUMENTS

| | | | |
|---|---|---|---|
| 4,177,268 A | 12/1979 | Torossian et al. | |
| 5,646,160 A | 7/1997 | Morris et al. | |
| 5,658,940 A | 8/1997 | Muller et al. | |
| 5,990,176 A | 11/1999 | Bieniarz et al. | |
| 6,015,815 A | 1/2000 | Mollison | |
| 6,074,668 A | 6/2000 | Flament-Garcia et al. | |
| 6,083,514 A | 7/2000 | Chang et al. | |
| 6,096,070 A | 8/2000 | Ragheb et al. | |
| 6,162,443 A | 12/2000 | Flament-Garcia et al. | |
| 6,288,127 B1 | 9/2001 | Bieniarz et al. | |
| 6,304,786 B1 * | 10/2001 | Heil et al. | 607/126 |
| 6,329,386 B1 | 12/2001 | Mollison | |
| 6,444,859 B2 | 9/2002 | Bieniarz et al. | |
| 6,503,556 B2 | 1/2003 | Pacetti et al. | |
| 6,558,679 B2 | 5/2003 | Flament-Garcia et al. | |
| 6,585,764 B2 | 7/2003 | Wright et al. | |
| 6,677,492 B2 | 1/2004 | Bieniarz et al. | |
| 6,743,462 B1 | 6/2004 | Pacetti | |
| 6,890,546 B2 | 5/2005 | Mollison et al. | |
| 6,896,965 B1 | 5/2005 | Hossainy | |
| 6,908,624 B2 | 6/2005 | Hossainy et al. | |
| 7,087,263 B2 | 8/2006 | Hossainy et al. | |
| 7,202,325 B2 | 4/2007 | Pacetti et al. | |
| 7,208,190 B2 | 4/2007 | Verlee et al. | |
| 7,214,759 B2 | 5/2007 | Pacetti et al. | |
| 7,232,573 B1 | 6/2007 | Ding | |
| 7,247,313 B2 | 7/2007 | Roorda et al. | |
| 7,247,364 B2 | 7/2007 | Hossainy et al. | |
| 7,261,946 B2 | 8/2007 | Claude | |
| 7,279,174 B2 | 10/2007 | Pacetti et al. | |
| 7,285,304 B1 | 10/2007 | Hossainy et al. | |
| 7,294,329 B1 | 11/2007 | Ding | |
| 7,357,793 B2 | 4/2008 | Pacetti | |
| 7,357,942 B2 | 4/2008 | Burke et al. | |
| 7,361,726 B2 | 4/2008 | Pacetti et al. | |
| 7,378,105 B2 | 5/2008 | Burke et al. | |
| 7,378,106 B2 | 5/2008 | Hossainy et al. | |
| 7,390,497 B2 | 6/2008 | DesNoyer et al. | |
| 7,396,541 B2 | 7/2008 | Hossainy et al. | |
| 7,399,480 B2 | 7/2008 | Mollison et al. | |
| 7,413,746 B2 | 8/2008 | Ding | |
| 7,431,959 B1 | 10/2008 | Dehnad | |
| 7,438,722 B1 | 10/2008 | Hossainy | |
| 7,445,792 B2 | 11/2008 | Toner et al. | |
| 7,491,233 B1 | 2/2009 | Ding et al. | |
| 7,494,665 B1 | 2/2009 | Ding et al. | |
| 7,520,891 B2 | 4/2009 | DesNoyer et al. | |
| 2001/0027340 A1 | 10/2001 | Wright et al. | |
| 2002/0133183 A1 | 9/2002 | Lentz et al. | |
| 2005/0208093 A1 | 9/2005 | Glauser et al. | |
| 2005/0238686 A1 | 10/2005 | Hossainy et al. | |
| 2005/0245637 A1 | 11/2005 | Hossainy et al. | |
| 2005/0265960 A1 | 12/2005 | Pacetti et al. | |
| 2005/0266038 A1 | 12/2005 | Pacetti et al. | |
| 2005/0271700 A1 | 12/2005 | Pacetti et al. | |
| 2006/0002977 A1 | 1/2006 | Dugan | |
| 2006/0115513 A1 | 6/2006 | Pacetti et al. | |
| 2006/0134165 A1 | 6/2006 | Pacetti | |
| 2006/0136048 A1 | 6/2006 | Pacetti et al. | |
| 2006/0147412 A1 | 7/2006 | Pacetti et al. | |
| 2006/0198867 A1 | 9/2006 | Toner et al. | |
| 2006/0198870 A1 | 9/2006 | Mollison et al. | |
| 2006/0216326 A1 | 9/2006 | Pacetti | |
| 2006/0228452 A1 | 10/2006 | Cromack et al. | |
| 2006/0246108 A1 | 11/2006 | Pacetti et al. | |
| 2006/0246109 A1 * | 11/2006 | Hossainy et al. | 424/426 |

(Continued)

FOREIGN PATENT DOCUMENTS

EP   0 778 250   6/1996

(Continued)

OTHER PUBLICATIONS

Wikipedia, Analog, pp. 1-2, accessed Oct. 4, 2010.*
U.S. Appl. No. 10/816,072, filed Mar 31, 2004, Dugan et al.
U.S. Appl. No. 10/913,607, filed Aug. 5, 2004, Pacetti et al.
U.S. Appl. No. 11/437,075, filed May 18, 2006, Pacetti et al.
U.S. Appl. No. 11/820,560, filed Jun. 19, 2007, Pacetti et al.
U.S. Appl. No. 11/832,568, filed Aug. 1, 2007, Hossainy et al.
U.S. Appl. No. 11/836,032, filed Aug. 8, 2007, Pacetti.
U.S. Appl. No. 11/864,472, filed Sep. 28, 2007, Huang et al.
U.S. Appl. No. 11/891,150, filed Aug. 8, 2007, Pacetti et al.
U.S. Appl. No. 12/108,440, filed Apr. 23, 2008, Pacetti.
U.S. Appl. No. 12/124,991, filed May 21, 2008, Pacetti et al.

(Continued)

*Primary Examiner* — Kevin Hill
*Assistant Examiner* — Lyndsey Beckhardt
(74) *Attorney, Agent, or Firm* — Squire, Sanders & Dempsey (US) LLP

(57) ABSTRACT

The present invention encompasses a coating on the surface of a substrate and the coated substrates. The coating includes a polymer, an olimus drug (sirolimus, everolimus, zotarolimus, etc.), and a dexamethasone derivative. The polymer may be a hydrophobic polymer, preferably a fluoropolymer, and more preferably a fluoropolymer with at least 25% vinylidene fluoride by weight.

17 Claims, 8 Drawing Sheets

U.S. PATENT DOCUMENTS

| | | | |
|---|---|---|---|
| 2007/0009565 A1 | 1/2007 | Pacetti et al. | |
| 2007/0020312 A1 | 1/2007 | Pacetti et al. | |
| 2007/0022424 A1 | 1/2007 | Heirich | |
| 2007/0128246 A1 | 6/2007 | Pacetti et al. | |
| 2007/0190103 A1 | 8/2007 | Pacetti et al. | |
| 2007/0202147 A1 | 8/2007 | Kleiner et al. | |
| 2007/0202323 A1 | 8/2007 | Kleiner et al. | |
| 2007/0224240 A1* | 9/2007 | Toner et al. | 424/423 |
| 2007/0231851 A1 | 10/2007 | Toner et al. | |
| 2007/0280991 A1 | 12/2007 | Glauser et al. | |
| 2008/0003254 A1 | 1/2008 | Mack et al. | |
| 2008/0004694 A1 | 1/2008 | Mack et al. | |
| 2008/0014245 A1 | 1/2008 | Pacetti et al. | |
| 2008/0020129 A1 | 1/2008 | Verlee et al. | |
| 2008/0044675 A1 | 2/2008 | Ding | |
| 2008/0087283 A1 | 4/2008 | Cromack et al. | |
| 2008/0145402 A1 | 6/2008 | Mollison et al. | |
| 2008/0153790 A1 | 6/2008 | Mollison et al. | |
| 2008/0171763 A1 | 7/2008 | Mollison et al. | |
| 2008/0175884 A1 | 7/2008 | Mollison et al. | |
| 2009/0004243 A1 | 1/2009 | Pacetti et al. | |
| 2009/0104241 A1 | 4/2009 | Pacetti et al. | |
| 2009/0104247 A1 | 4/2009 | Pacetti et al. | |

FOREIGN PATENT DOCUMENTS

| | | |
|---|---|---|
| EP | 1 795 185 | 6/2007 |
| WO | WO 94/09010 | 4/1994 |
| WO | WO 2005/081655 | 9/2005 |

OTHER PUBLICATIONS

U.S. Appl. No. 12/147,442, filed Jun. 26, 2008, Pacetti et al.
U.S. Appl. No. 12/165,173, filed Jun. 30, 2008, Ngo et al.
U.S. Appl. No. 12/165,521, filed Jun. 30, 2008, Lim et al.
U.S. Appl. No. 12/205,577, filed Sep. 5, 2008, Pacetti et al.
U.S. Appl. No. 10/240,917, filed Sep. 29, 2008, Pacetti et al.
Blindt et al. "A Novel Drug-Eluting Stent Coated with an Integrin-Binding Cyclic Arg-Gly-Asp peptide Inhibits Neointimal Hyperplasia by Recruiting Endothelial Progenitor Cells", J. of the Am. College of Cardiology vol. 47, No. 9, pp. 1786-1795 (2006).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Lee et al., In-vivo *biocompatibility evaluation of stents coated with a new biodegradable elastomeric and functional polymer*, Coron. Artery. Dis., 13(4): (2002) pp. 237-241.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
International Search Report for PCT/US2009/057033, mailed Oct. 14, 2010, 17 pgs.

* cited by examiner

COATINGS INCLUDING DEXAMETHASONE DERIVATIVES AND ANALOGS AND OLIMUS DRUGS

FIELD

This invention relates to the field of implantable medical devices (IMDs), more particularly to implantable medical devices having a coating from which drug(s) can be released at a target site in patient's body, and still more particularly to coatings including olimus drugs and dexamethasone derivatives and analogs.

BACKGROUND

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective, and having evolved to a relatively high degree of safety for such an invasive procedure, by-pass surgery still involves serious potential complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, PCTA failed to satisfactorily ameliorate another problem, restenosis, the re-clogging of the treated artery.

The next improvement, advanced in the mid-1980s was use of a stent to scaffold the vessel walls open after PTCA. This for all intents and purposes put an end to elastic recoil but did not entirely resolve the issue of restenosis. That is, prior to the introduction of stents, restenosis occurred in from 30-50% of patients undergoing PTCA. Stenting reduced this to about 15-30%, much improved, but still more than desirable.

In 2003, the drug-eluting stent (or DES) was introduced. The drugs initially employed with the DES were cytostatic compounds, compounds that curtailed the proliferation of cells that contributed to restenosis. As a result, restenosis was reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the superficial femoral artery.

An improvement in the DES is the multiple-drug DES.

SUMMARY

The current invention is directed to coatings for substrates, particularly coated implantable medical devices, and methods of treatment using the devices.

Thus, in one aspect, the present invention relates to a medical device including a device body with an outer surface, and a coating. The coating includes one or more coating layers disposed over the surface, a hydrophobic polymer, an olimus drug, and a dexamethasone derivative or analog. The dexamethasone derivative or analog in the coating is substantially amorphous.

Thus, in another aspect, the present invention relates to a method of treating a medical condition in a patient by implanting in a patient in need thereof a coated device as described in the previous.

In an aspect of this invention, the olimus drug dose is between about 10 and about 600 $\mu g/cm^2$ and the dose of dexamethasone derivative or analog is between 10 and about 600 $\mu g/cm^2$.

In an aspect of this invention, one coating layer comprises the olimus drug and the dexamethasone derivative or analog.

In an aspect of this invention, the mass ratio of olimus drug to dexamethasone derivative or analog is between about 1:1 and about 1:4.

In an aspect of this invention, the device is an implantable medical device.

In an aspect of this invention, the implantable medical device is a stent.

In an aspect of this invention, the device is a catheter balloon.

In an aspect of this invention, the hydrophobic polymer is a fluoropolymer.

In an aspect of this invention, the hydrophobic polymer is a fluoropolymer comprising at least 25% vinylidene fluoride by weight.

In an aspect of this invention, the hydrophobic polymer is PVDF-HFP.

In an aspect of this invention, the olimus drug is selected from the group consisting of sirolimus, everolimus, zotarolimus, biolimus A9, novolimus, temsirolimus, AP23572, and combinations thereof.

In an aspect of this invention, the dexamethasone derivative or analog is a compound of the formula, or any combination of compounds represented by the formula:

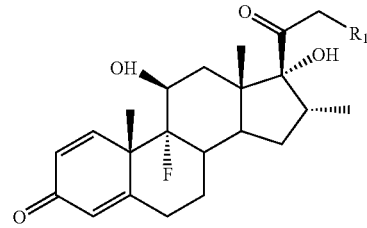

wherein R1 may be selected from the group the consisting of

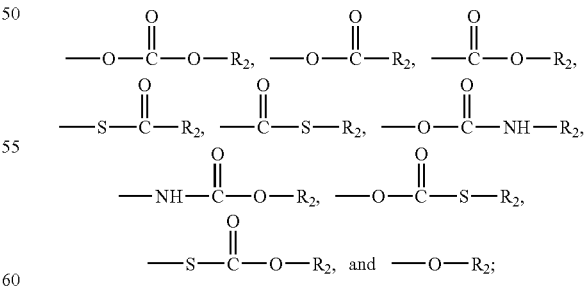

wherein $R_2$ is selected from the group consisting of (C1-C16) alkyl, (C2-C16)alkenyl, (C2-C16)alkynyl, (C3-C10)cycloalkyl, phenyl, ester, carbonate, ether, and ketone. Any one or more hydrogen atoms on the cycloalkyl or aromatic ring is optionally substituted with a substituent selected from the group consisting of alkyl, alkenyl, and alkynyl, and any one or more hydrogen atoms on $R_2$ are optionally replaced with chlorine, fluorine or a combination thereof. The total number of carbon atoms in $R_2$ is not more than 16.

In an aspect of this invention, the dexamethasone derivative or analog is a compound of the formula, or any combination of compounds represented by the formula:

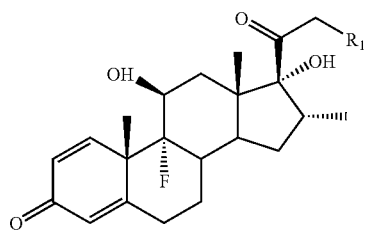

wherein R1 may be selected from the group the consisting of

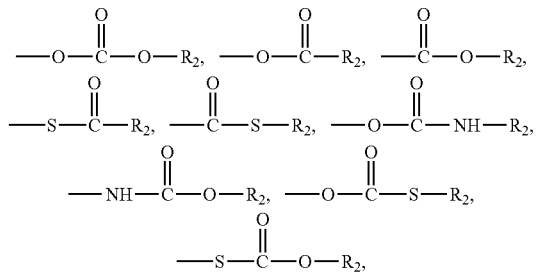

and -o-$R_2$; and wherein $R_2$ is selected from the group consisting of methyl, ethyl, n-propyl, n-butyl, tert-butyl, n-pentyl, n-hexyl, phenyl, benzyl, pentadecane ($C_{15}H_{31}$), tetrahydrophthalate, 4-pyridinium, diethylaminomethylene, and metasulfobenzoate.

In an aspect of this invention, the dexamethasone derivative or analog is selected from the group consisting of dexamethasone acetate, dexamethasone palmitate, dexamethasone diethylaminoacetate, dexamethasone isonicotinate, dexamethasone tert-butylacetate, dexamethasone tetrahydrophthalate, and combinations thereof.

In an aspect of this invention, the dexamethasone derivative or analog is dexamethasone acetate.

In an aspect of this invention, the cumulative drug release of the olimus drug is not more than 50% of the total olimus drug content at 24 hours.

In an aspect of this invention, the cumulative drug release of the dexamethasone derivative or analog is not more than 50% of the total dexamethasone derivative or analog drug content at 24 hours.

In an aspect of this invention, the coating includes zotarolimus and dexamethasone acetate.

In another aspect, the coating includes everolimus and/or zotarolimus and dexamethasone acetate. The cumulative drug release of the dexamethasone acetate is not more than 50% of the total dexamethasone acetate content at 24 hours, and the cumulative drug release of the zotarolimus and/or everolimus is not more than 50% of the total zotarolimus and/or everolimus content at 24 hours.

In an aspect of this invention, the medical condition to be treated is selected from restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

DISCUSSION

Figure 1A:
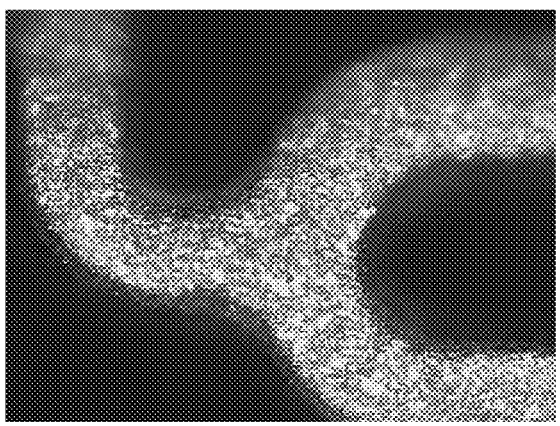
FIGS. 1A and 1B depict a coated stent after sterilization at magnifications of 200 and 500, respectively.

The present invention encompasses a coating disposed over the surface of a substrate, the coated substrates, and methods of treatment utilizing coated medical devices. The coating includes a polymer, an olimus drug, and a drug selected from dexamethasone derivatives and analogs. The polymer may be a hydrophobic polymer, preferably a fluoropolymer, and more preferably a fluoropolymer with at least 25% vinylidene fluoride by weight.

As outlined above, DES has been introduced to help reduce restenosis. A number of cellular mechanisms have been proposed that lead to restenosis of a vessel. Two of these mechanisms are (1) the migration and proliferation of smooth muscle cells to and at the site of injury, and (2) the acute and chronic inflammatory response to injury and foreign body presence.

Stenting of an artery may lead to vascular injury. This is partially due to mechanical injury induced by stent implantation that can cause endothelial denudation and vessel injury. Endothelial denudation is directly associated with the formation of lesions in the vessel wall which may incite an inflammatory response. When inflamed, the endothelial cells that line the blood vessels produce substances called chemokines that attract neutrophils, monocytes, and other white blood cells to the site of injury. Swelling of endothelial cells disrupts the tight connections between the endothelial cells, allowing neutrophils and monocytes to transmigrate into the surrounding tissue. The subsequent recruitment of neutrophils and monocytes into the tissue is a normal part of the healing process. However, if the inflammation becomes chronic the prolonged residence of neutrophils, macrophages, and lymphocytes can actually inhibit healing and exacerbate the tissue damage from the original injury. When tissue repair occurs it can be dysregulated, and when combined with prolonged inflammation, this may lead to excessive neointimal formation and scarring.

Vulnerable plaque (VP) refers to a fatty build-up in an artery thought to be caused by chronic atherosclerotic disease combined with an accumulation of lipid and foam cells in the vessel wall. The VP is covered by a thin fibrous cap that can rupture leading to blood clot formation. Since sites of VP have a higher density of macrophages and lymphocytes than other types of atherosclerotic lesions, it is expected that these sites, when stented, will produce elevated amounts of the cytokines (IL-1, TNF-alpha) that promote smooth muscle cell proliferation. Previous animal (porcine) studies have demonstrated that inflammation promotes proliferation at sites of balloon angioplasty and stent placement (Kornowski, et al., Coron Artery Dis. 12(6):513-5 (2001)).

To reduce cell proliferation, some DES include a cytotoxic compound. Paclitaxel, a cytotoxic compound, is expected to potently inhibit endothelial migration and re-endothelialization potentially resulting is a delayed healing response (U.S. Patent Application publication 2008/0004694, incorporated by reference, as fully set forth including drawings, herein). In contrast, it has been shown that dexamethasone has a positive effect on endothelial migration and may promote vascular healing when administered to the lumen of a vessel. Paclitaxel and zotarolimus, but not dexamethasone, inhibit endothelial cell proliferation. Furthermore, paclitaxel, but not zotarolimus or dexamethasone, inhibits migration of human coronary artery endothelial cells in vitro. Compared to paclitaxel, a combination of dexamethasone and zotarolimus are predicted to have less inhibition for re-endothelialization of vascular regions.

Addition of an anti-inflammatory drug to an olimus drug such as zotarolimus will suppress the inflammatory response to stent implantation more than is the case when stents are implanted carrying only an olimus drug. In cases where the inflammation is above that required for normal healing, and chronic, addition of the anti-inflammatory drug may assist with healing. The inflammatory response itself exacerbates the neointimal growth. Activated platelets, machrophages and neutrophils all secrete pro-growth cytokines. A dual drug system with both an olimus drug and an anti-inflammatory drug can have a more profound anti-restenonitc effect than just an olimus drug alone due to the inhibition of multiple pathways for neointimal growth. This attribute can be leveraged for improved healing by reducing the dose of the olimus drug or duration of drug release while still maintaining a high level of efficacy.

Therefore, a combination of dexamethasone and zotarolimus in a single DES would be advantageous, and a combination of both in a single coating layer would be even more advantageous.

Multiple drug DES present a challenge. A DES including everolimus has been approved for use in the United States, but addition of dexamethasone to this coating results in significant dexamethasone crystallization within the polymer coating. Dexamethasone belongs to the glucocorticoid or steroidal family of drugs. This family, as a whole, has a strong propensity to crystallize. This is driven by the flat and rigid, four member ring structure which gives the molecule little internal degrees if freedom and allows them to stack very efficiently. The high melting points for this class of compounds is an indicator of the thermodynamic stability of the crystals formed. Crystallization of the drug within the coating may impact release rate. It is believed that crystals on the surface may also potentially pose an embolic hazard. Moreover, crystals on the surface pose aesthetic issues. As only a portion of the dexamethasone may crystallize, a change in degree of crystallinity with time can create a stability issue. A DES containing dexamethasone may be manufactured utilizing a polymer with some hydrophilic groups. However, use of such a polymer in a coating results in quick release of the dexamethasone.

It has been found that a more lipophilic derivative of or analog of dexamethasone in combination with everolimus (or zotarolimus) when used at the appropriate mass percent of drug in a coating layer including a hydrophobic polymer leads to lower levels of crystallization than the combination of dexamethasone and everolimus. With the more lipophilic dexamethasone derivative or analog, the driving force for the drug to crystallize is reduced in hydrophobic polymers. This is due to the increased solubility of the lipophilic dexamethasone derivative or analog in the polymer. The improved compatibility is maintained even after sterilization of the device with ethylene oxide. Additionally, the hydrophobic polymer provides for the controlled release of both the olimus drug and the dexamethasone derivative or analog.

For the purposes of this invention, the coatings may be applied to a number of substrates of which a stent is an example. Although reference may be made to "an olimus drug," "a dexamethasone derivative or analog," and "a polymer" when referring to coatings or coated substrates, embodiments of the present invention encompass one or more olimus drugs, one or more of the group of dexamethasone derivatives and analogs, and one or more polymers. In some embodiments, clinical efficacy is obtained by the use of a combination of drugs where the dose of each of the individual drugs in the combination would not be clinically efficacious if used alone.

Definitions

As used herein, unless specified otherwise, any words of approximation such as, without limitation, "about," "essentially," "substantially" and the like mean that the element so modified need not be exactly what is described but can vary from the description by as much as ±5% without exceeding the scope of this invention.

As used herein, a "drug," refers to any substance that, when administered in a therapeutically effective amount to a patient suffering from a disease or condition, has a therapeutic beneficial effect on the health and well-being of the patient. A therapeutic beneficial effect on the health and well-being of an individual includes, but is not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "drug," also refers to pharmaceutically acceptable, pharmacologically active derivatives of those drugs specifically mentioned herein, including, but not limited to, salts, esters, amides, and the like.

As used herein, a material that is described as "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably herein. As used herein, the term "coating" refers to one or more layers deposited on a substrate.

As used herein, "negligible levels of crystals" and "negligible crystallization" mean that the visible crystals number 100 or fewer per cm$^2$, or alternatively, the percent of the drug crystallized, as determined by X-ray crystallography, differential scanning calorimetry, solid state NMR, or IR analysis, if appropriate, is about 10% or less. Inspection of the device by reflectance microscopy with crossed polarizers is an effective method to visual the drug crystals. By this method, the crystals shine brightly making them amenable to quantification by manual counting or by image analysis.

Dexamethasone Derivatives and Analogs

Embodiments of the present invention encompass dexamethasone derivatives and analogs that are more lipophilic than dexamethasone, and any combination of these dexamethasone derivatives and analogs.

Dexamethasone is a compound of the following formula:

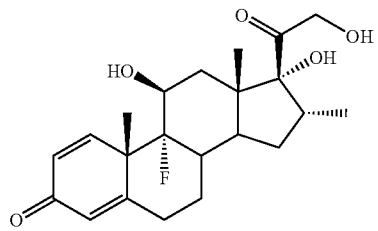

Dexamethasone has a molecular weight of 392.45 and a melting point of around 262 to 264° C.

As used herein, the term "dexamethasone derivatives and analogs" encompasses compounds of the following formula:

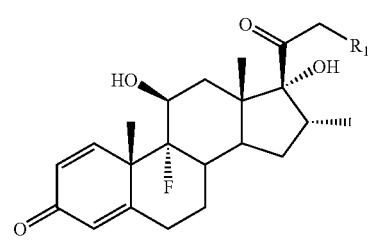

where the $R_1$ is one of the following:

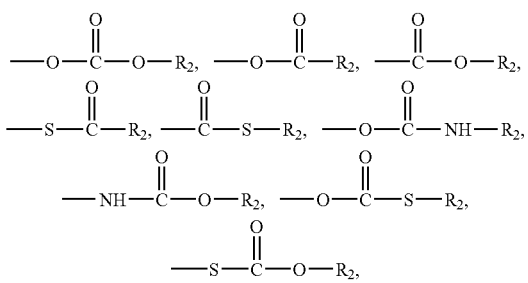

or —O—$R_2$, and where $R_2$ may be a hydrophobic moiety as outlined below.

As used herein, "alkyl" refers to a straight, branched chain fully saturated (no double or triple bonds) hydrocarbon group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —CH$_2$—, ethylene, —CH$_2$CH$_2$—, propylene, —CH$_2$CH$_2$CH$_2$—, n-butylene, —CH$_2$CH$_2$CH$_2$CH$_2$—, sec-butylene, —CH$_2$CH$_2$CH(CH$_3$)— and the like.

As used herein, "Cm to Cn," wherein m and n are integers refers to the number of possible carbon atoms in the indicated group. That is, the group can contain from "m" to "n", inclusive, carbon atoms. For instance without limitation, an alkyl group of this invention may consist of 3 to 8 carbon atoms, in which case it would be designated as a (C3-C8)alkyl group. The numbers are inclusive and incorporate all straight or branched chain structures having the indicated number of carbon atoms. For example without limitation, a "C1 to C4 alkyl" group refers to all alkyl groups having from 1 to 4 carbons, that is, CH$_3$—, CH$_3$CH$_2$—, CH$_3$CH$_2$CH$_2$—, CH$_3$CH(CH$_3$)—, CH$_3$CH$_2$CH$_2$CH$_2$—, CH$_3$CH$_2$CH(CH$_3$)— and (CH$_3$)$_3$CH—.

As use herein, a cycloalkyl group refers to an alkyl group in which the end carbon atoms of the alkyl chain are covalently bonded to one another. The numbers "m" and "n" refer to the number of carbon atoms in the ring formed. Thus for instance, a (C3-C8) cycloalkyl group refers to a three, four, five, six, seven or eight member ring, that is, cyclopropane, cyclobutane, cyclopentane, cyclohexane, cycloheptane and cyclooctane.

As used herein, "alkenyl" refers to a hydrocarbon group that contains one or more double bonds.

As used herein, "alkynyl" refers to a hydrocarbon group that contains one or more triple bonds.

As used herein, "aromatic" refers to a hydrocarbon compound which comprises a benzene ring, which is represented by

.

Standard shorthand designations well-known to those skilled in the art are used throughout this application. Thus the intended structure will easily be recognizable to those skilled in the art based on the required valence of any particular atom with the understanding that all necessary hydrogen atoms are provided. For example, —COR or —C(O)R, because carbon is tetravalent, must refer to the structure

as that is the only way the carbon can be tetravalent without the addition of hydrogen or other atoms no shown in the structure.

Likewise, it is understood by those skilled in the chemical arts that so-called stick structure, exemplified by

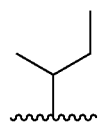

represents the structure

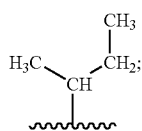

that is, each terminus is capped with a $CH_3$ group and the apex of each angle is a carbon atom with the requisite number of hydrogen atoms attached.

The $R_2$ moiety of the $R_1$ substituent above may be any moiety containing hydrogen, carbon, and oxygen, but if oxygen is present it is part of an ester

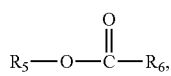

an ether (—$R_5$—O—$R_6$), a carbonate

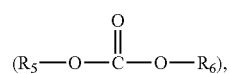

and/or a ketone

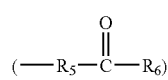

wherein the $R_5$ and $R_6$ substituents each contain at least one carbon atom which is connected to the ester, carbonate, and ketone groups (that is $R_5$ and $R_6$ are not H or —OH). The total number of carbon atoms in the $R_2$ moiety is not more than 16.

The $R_2$ moiety can be a hydrocarbon containing between 1 and 16 carbons including a saturated hydrocarbon such as a C1-C16 alkyl, or unsaturated hydrocarbon, that is a C2-C16 alkenyl, a C2-C16 alkynyl, or a moiety containing both double and triple carbon-carbon bonds. The $R_2$ moiety may be a branched or straight chain. The $R_2$ moiety may include a cycloaliphatic, such as a C3-C10 cycloalkyl, an aromatic group, and/or another hydrocarbon ring structure containing one or more double and/or one or more triple carbon-carbon bonds. One or more substituent groups may optionally be attached to a ring.

If the $R_2$ moiety includes a ring, then the ring may connect to the

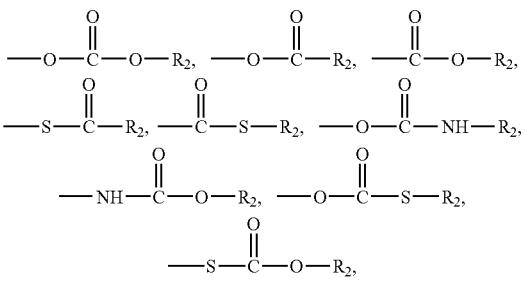

or -o-$R_2$, directly or via a substituent group.

The above description of the $R_2$ moiety is also applicable to the $R_5$ and $R_6$ moieties, and any optional substituents on a ring, except that the number of carbon atoms in each is limited as the total number of carbon atoms in the $R_2$ moiety is not more than 16. Thus, there may be multiple ester, carbonate, and/or ketone groups present in a $R_2$ moiety, and any one or more of these may be present on a substituent group. In other words, the $R_5$ and $R_6$ moieties may also include one or more groups independently selected from ester, carbonate, and/or ketone, provided that on each side of each of the ester, carbonate, and/or ketone groups attach to a carbon atom. The substituents on the ring may form another ring.

The $R_2$ moiety may also be benzyl, tetrahydrophthalate, 4-pyridinium, diethylaminomethylene, or metasulfobenzoate.

In any of the possible $R_2$ moieties, one or more of the hydrogen atoms may be replaced with a halogen atom such as, without limitation, fluorine and/or chlorine.

Non-limiting examples of $R_2$ groups include the following:

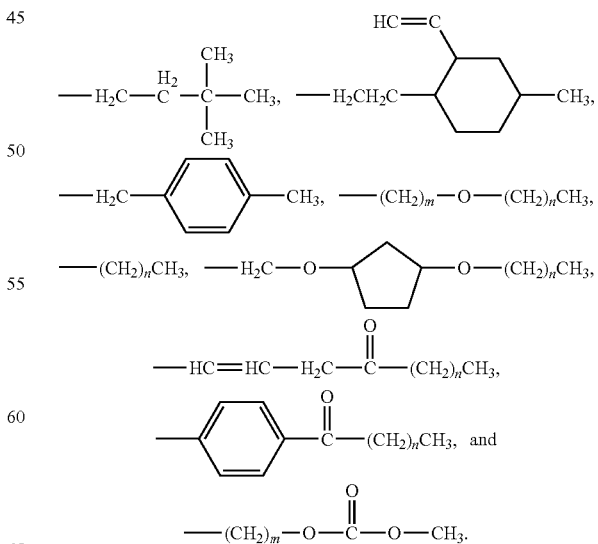

In the above examples, m and n represent integers.

A preferred list of $R_2$ moieties includes methyl, ethyl, n-propyl, n-butyl, tert-butyl, n-pentyl, n-hexyl, phenyl, benzyl, pentadecane ($C_{15}H_{31}$), tetrahydrophthalate, 4-pyridinium, diethylaminomethylene, and metasulfobenzoate.

As used here, the term "dexamethasone derivatives and analogs" also encompasses derivatives or analogs of dexamethasone with a solubility parameter less than or equal to 10 $(cal/cm^3)^{1/2}$.

As used herein, the term "dexamethasone derivatives and analogs" also encompasses the following specific compounds, without limitation:

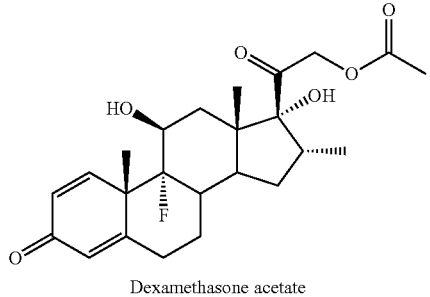

Dexamethasone acetate

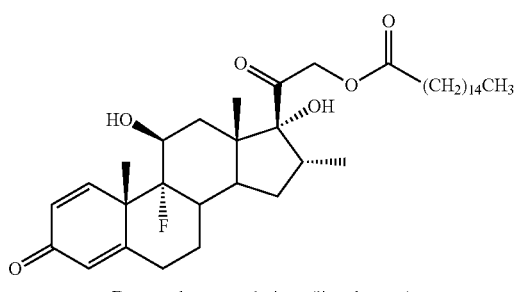

Dexamethasone palmitate (limethasone)

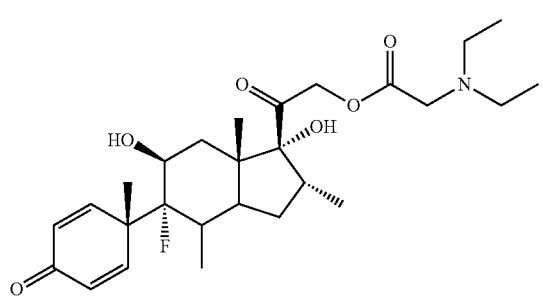

Dexamethasone diethylaminoacetate (SOLU-FORTE-CORTIN®)

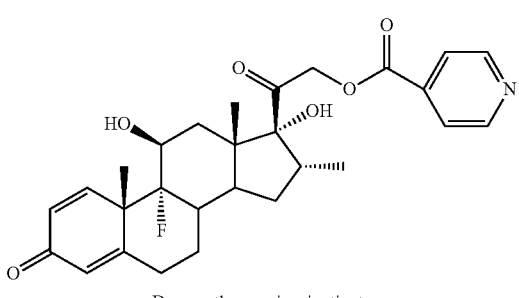

Dexamethasone isonicotinate

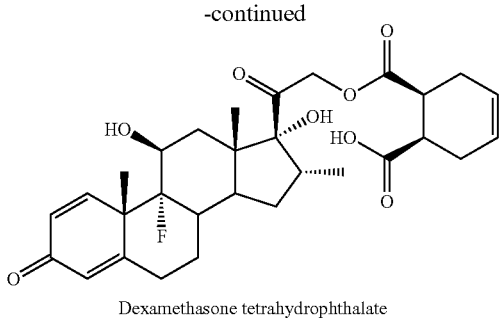

Dexamethasone tetrahydrophthalate

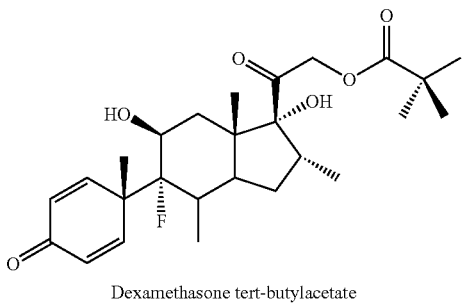

Dexamethasone tert-butylacetate

The dose of the dexamethasone derivative or analog may range from 10-600 μg/cm², preferably from 20 to 400 μg/cm², and more preferably from 30 to 200 μg/cm².

Olimus Drugs

Embodiments of the present invention include one or more olimus drugs.

As used herein, the term "olimus drug," refers to rapamycin (sirolimus) and its functional or structural derivatives. These derivatives include, without limitation: Biolimus A9 (Biosensors International, Singapore), deforolimus, AP23572 (Ariad Pharmaceuticals), tacrolimus, temsirolimus, pimecrolimus, novolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazolylrapamycin, and 40-epi-(N1-tetrazolyl)-rapamycin. Also included in olimus drugs are those compounds with a substituent at the carbon corresponding to the 42 or 40 carbon of rapamycin.

The dose of the olimus drug may range from 10-600 μg/cm², preferably from 20 to 400 μg/cm², and more preferably from 30 to 200 μg/cm².

Hydrophobic Polymers

Embodiments of the present invention encompass one or more hydrophobic polymers. Also polymers that are not characterized as "hydrophobic polymers" may also be included in the coatings of the present invention.

As used herein, a "polymer" is a molecule made up of the repetition of a simpler unit, herein referred to as a "constitutional unit," wherein the constitutional units derive from the reaction of monomers. A non-limiting example, $CH_2=CH_2$ or ethylene, is a monomer that can be polymerized to form polyethylene, such as $CH_3(CH_2)_nCH_3$, wherein the constitutional unit is —$CH_2$—$CH_2$—, ethylene having lost the double bond as a result of the polymerization reaction. A polymer of this invention may be derived from the polymerization of several different monomers and therefore may comprise several different constitutional units. Such polymers are referred to as "copolymers." Those skilled in the art, given a particular polymer, will readily recognize the constitutional units of that polymer and will equal readily recognize the structure of the monomer from which the constitutional units derive. Polymers of this invention may be regular alternating polymers, random alternating polymers, regular block polymers, random block polymers or purely random polymers unless expressly noted otherwise. Polymers may be cross-linked for form a network.

As used herein, a "hydrophobic polymer" is one for which the water absorption by the polymer is not more than about 5% by weight, measured at or near at physiological conditions, that is at about 37° C., normal atmospheric pressure (about 1 atmosphere), and at about pH 7.4.

In some embodiments, the hydrophobic polymer used may be one for which the water absorption at 37° C. and normal atmospheric pressure is not more than 2% by weight, or more narrowly, not more than 1% by weight, or even more narrowly, not more than 0.5% by weight, or most narrowly, not more than 0.1% by weight.

In some embodiments, the hydrophobic polymer may be one with a solubility parameter less than or equal to about 11.5 $(cal/cm^3)^{1/2}$.

In some embodiments, the hydrophobic polymer is a fluoropolymer. A fluoropolymer is one that contains fluorine atoms, generally in locations where one or more hydrogen atoms would exist in the equivalent non-fluoropolymer. Some non-limiting examples of fluoropolymers include poly(vinylidene fluoride) ("PVDF"), poly(vinylidene fluoride-co-hexafluoropropene) ("PDVF-HFP"), poly(tetrafluoroethylene) ("PTFE," or TEFLON®), fluorinated poly(ethylene-co-propylene) ("FEP"), poly(hexafluoropropene), poly(chlorotrifluoroethylene) ("PCTFE"), poly(vinylidene fluoride-co-tetrafluoroethylene) ("PVDF-TFE"), poly(tetrafluoroethylene-co-hexafluoropropene), poly(tetrafluoroethylene-co-vinyl alcohol), poly(tetrafluoroethylene-co-vinyl acetate), poly(tetrafluoroethylene-co-propene), poly(hexafluoropropene-co-vinyl alcohol), poly(tetrafluoroethylene-co-fluoromethylvinyl ether), poly(ethylene-co-tetrafluoroethylene) ("ETFE"), poly(ethylene-co-hexafluoropropene), poly(vinylidene fluoride-co-chlorotrifluoroethylene), fluorinated silicones, perfluoroalkyl vinyl ether and tetrafluoroethylene co-polymer("PFA"), a copolymer of vinylidenedifluoride, hexafluoropropylene and tetrafluoroethylene("TFB"), polyvinylfluoride("PVF"), a copolymer of poly(tetrafluoroethylene) and fluoromethylvinyl ether, poly(vinylidene fluoride-co-chlorotrifluoroethylene), poly(vinylidene fluoride-co-ethylene), poly(vinylidene fluoride-co-tetrafluoroethylene), poly(tetrafluoroethylene-co-ethylene), poly(vinylidene fluoride-co-trifluoroethylene) ("PVDF-TrFE"), and poly(vinylidene fluoride-co-tetrafluoroethylene). Other fluoropolymers include a fluoroalkoxyl-containing polymer, a mixture of silicone and a fluoropolymer. Any combination of the above listed fluoropolymers may be used.

Preferred classes of polymers are fluoropolymers including at least 25% by weight of vinylidene fluoride, and the PDVF-HFP copolymers. A more preferred group of polymers is PDVF-HFP polymers with at least 25% by weight of vinylidene fluoride.

Coating Constructs

As used herein, a "primer layer" refers to a coating layer including a polymer or blend of polymers that exhibit good adhesion characteristics with regard to the material of which the substrate is manufactured and whatever material is to be coated on the substrate. Thus, a primer layer serves as an adhesive intermediary layer between a substrate and materials to be carried by the substrate and is, therefore, applied directly to the substrate.

As used herein, "drug reservoir layer" refers to a layer that includes one or more drugs. The layer may comprise one or more drugs applied neat, applied with an excipient such as a binder, or as a component of a polymer matrix. A polymeric drug reservoir layer is designed such that, by one mechanism or another, e.g., without limitation, by elution or as the result of biodegradation of the polymer, the drug is released from the layer into the surrounding environment.

Embodiments of the present invention encompass coating constructs which include a hydrophobic polymer, a dexamethasone derivative or analog, and an olimus drug in one coating layer, to be referred to herein as a "DD/OD drug reservoir layer." In some embodiments, the DD/OD drug reservoir layer is the only coating layer on the substrate, while in a preferred embodiment there is a primer layer in addition to the DD/OD drug reservoir layer. In some embodiments, the olimus drug and the dexamethasone derivative or analog may be applied in separate coating layers each of which optionally include one or more polymers. The olimus drug and/or the dexamethasone derivative or analog may be applied in one or two non-polymeric drug reservoir layers with a layer including a hydrophobic polymer above these layer(s). The layer above may be a layer including an olimus drug and/or a drug from the group of dexamethasone derivatives and analogs, and/or the layer may be a DD/OD drug reservoir layer.

Embodiments of the invention include one or more drug reservoir layers, any number (including zero) of coating layers below the drug reservoir layer(s), any number of layers above the drug reservoir layer(s), any number of coating layers between the multiple drug reservoir layers, if more than one drug reservoir layer, and any combination of the above.

Any layer may optionally contain another drug other than an olimus drug and/or dexamethasone derivative or analog, including any drug reservoir layer that includes an olimus drug and/or a drug in the group of dexamethasone derivatives and analogs. For multiple drug reservoir layers, there may be different types of polymers, olimus drugs, and/or different drugs from the group of dexamethasone derivatives and analogs used in the different layers.

The mass percent of olimus drug in the drug reservoir layer may be from about 2% to about 90% if the drug reservoir layer includes a polymer, preferably from about 4% to about 50% by mass, and more preferably from 5% to 25% by mass.

The mass percent of dexamethasone derivative or analog in the drug reservoir layer may be from about 1% to about 90% if the drug reservoir layer includes a polymer, preferably from about 2% to about 50% by mass, and more preferably from about 4% to about 20% by mass.

For non-polymeric drug reservoir layers, the mass percent of either olimus drug, dexamethasone derivative or analog, and/or the combination thereof, may be about 100%, or may be from about 75% to about 100%, preferably from about 50% to about 90% by mass, and more preferably from about 10% to about 75% by mass.

The mass percent of hydrophobic polymer in the drug reservoir layer may be from about 10% to about 98% by mass, with a preferred range from 30% to 90%, and a more preferred range from about 50% to about 85%. In some embodiments, the drug reservoir layer includes essentially only polymer and drug(s). In other embodiments, polymer and drug(s) are at least 80% or at least 90% by weight of the drug reservoir layer.

Embodiments of the present invention encompass a total coating thickness from 0.2 microns to 50 microns, preferably 0.5 microns to 25 microns, and more preferably 1 micron to 15 microns. For an individual coating layer, the thickness may range from 0.2 microns to 50 microns, preferably 0.5 microns to 25 microns, and more preferably 1 micron to 15 microns.

In some embodiments, the coating may be disposed over all, or substantially all, of the surface of the substrate, such as the outer surface of the device body of an implantable medical device. In some embodiments of the present invention, the coating may be disposed over only part of or portions of the substrate. As a non-limiting example, the abluminal or the luminal side of a stent may be selectively coated.

Improved Compatibility

As noted above, it is believed that an implantable medical device including both dexamethasone and everolimus (or zotarolimus or another olimus drug) provides clinical advantages. Also as noted in Example 7, in a 28-day safety study in domestic farm swine ("pigs"), a stent including both zotarolimus and dexamethasone acetate exhibited a lower extent of stenosis than a control DES consisting of the same stent platform coated with the same polymer but only containing the drug everolimus.

Embodiments of the present invention encompass a drug to polymer ratio in the range of about 1:1 to about 1:6 on a mass basis, or more preferably from about 1:1.5 to about 1:5, or most preferably from about 1:2.3 to about 1:4 in a drug reservoir layer, including a DD/OD drug reservoir layer. The drug to polymer ratio as used herein refers to the ratio of the total drug that is the sum of the one or more olimus drugs and the one or more drugs selected from the group of dexamethasone derivatives and analogs, to the total polymer in the layer.

As noted above, it has been found that a sub-set of dexamethasone derivatives and analogs, if used along with an olimus drug such as everolimus or zotarolimus in one coating layer with a hydrophobic polymer, allows for the production of a coating layer having a dexamethasone derivative or analog that is substantially amorphous.

As used herein, "substantially amorphous" refers about 10% crystallinity or less as measured by X-ray crystallography, differential scanning calorimetry, solid state NMR, or IR analysis measured at the time of use, such as, for example, the time of deployment or implantation for an implantable medical device.

The mass ratio of the olimus drug to the dexamethasone derivative or analog may be from 10:1 to 1:10, preferably from 6:1 to 1:6, and more preferably from 1:2 to 1:4. The molar ratio of the olimus drug to the dexamethasone derivative or analog may be from 5:1 to 1:25, preferably from 2:1 to 1:12, and more preferably from 1:3 to 1:9.

In some embodiments, a DD/OD drug reservoir exhibits an extent of crystallization of not more than 25% by weight of the dexamethasone derivative or analog present, preferably not more than 15% by weight, and preferably, negligible crystallization.

During ethylene oxide sterilization, the medical device is exposed to gas phase ethylene oxide that sterilizes through an alkylation reaction that prevents organisms from reproducing. Ethylene oxide penetrates the device, and then the device is aerated to assure very low residual levels of ethylene oxide because it is highly toxic. Thus, the ethylene oxide sterilization is often performed at elevated temperatures to speed up the process.

The combination of elevated temperature, humidity and ethylene oxide gas during ETO sterilization may impact drug recrystallization. Elevated temperature can increase the kinetics of drug recrystallization or elevate the coating above its glass transition temperature ($T_g$). In the rubbery phase, the kinetics of drug crystallization can be accelerated. Moisture can also plasticize some polymers which are not hydrophobic, while ethylene oxide can plasticize many hydrophobic polymers. Water droplets on the coating surface can also act as nuclei for drug crystallization.

Thus, in some embodiments, a DD/OD drug reservoir exhibits an extent of crystallization of not more than 25% by weight of the dexamethasone derivative or analog present, preferably of not more than 15% by weight, and more preferably, negligible crystallization after sterilization with ethylene oxide. In some embodiments, a DD/OD drug reservoir exhibits an extent of crystallization of not more than 25% by weight of the dexamethasone derivative or analog present, preferably of not more than 15% by weight, and more preferably, negligible crystallization, after sterilization with ethylene oxide at a temperature in the range of about 30 to about 55° C. and for a duration of about 2 to about 24 hours.

Release Rates

As illustrated in Example 6, the coating layers of the present invention allow for controlled release of both an olimus drug and a drug from the group of dexamethasone derivatives and analogs. A measure of the in vivo drug release rate may be accomplished in vitro by use of a biologically relevant medium, such as porcine serum, at 37° C. Thus, in some embodiments the olimus drug and the dexamethasone derivative or analog each have an in-vitro cumulative release (as measured for coated substrates in the unsterilized state) of not more than 50% of the total drug content at 24 hours, and the time period for 80% of the drug to be released is 7 days or longer. In a preferred embodiment, for each drug, the in-vitro release at 24 hours does not exceed 40% of the total drug content, and the time period for 80% of the drug to be released is 7 days or longer.

In some embodiments, each of the olimus drug and the dexamethasone derivative or analog have an in-vivo cumulative release (animal including human) of not more than 50% of the total drug content at 24 hours, and the time period for 80% of the drug to be released is 7 days or longer. In a preferred embodiment, for each drug, the in-vivo release at 24 hours does not exceed 40% of the total drug content and the time period for 80% of the drug to be released is 7 days or longer.

In some embodiments, only one of the two drugs may satisfy the above cumulative release criteria.

Substrates

The coatings included in the various embodiments of the present invention may be applied to any substrate for which a coating is beneficial or desirable. Preferred substrates are medical devices, and especially implantable medical devices.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, foramen ovale closure devices, cerebrospinal fluid shunts, orthopedic fixation devices, and intrauterine devices. While the preceding devices all have a primary function and, as a secondary function may be coated with a coating of this invention, an implantable medical device specifically designed and intended solely for the localized delivery of a drug is also within the scope of this invention.

A preferred implantable medical device is a stent. A stent refers generally to any device used to hold tissue in place in a patient's body. Particularly useful stents, however, are those used for the maintenance of the patency of a vessel in a patient's body when the vessel is narrowed or closed due to a diseases or disorder. For example, without limitation, a stent can be used to strengthen the wall of the vessel in the vicinity of the vulnerable plaque (VP) and act as a shield against rupture. As outlined above, VP is covered by a thin fibrous cap that can rupture leading to blood clot formation. A stent can be used in, without limitation, neuro, carotid, coronary, pulmonary, aorta, renal, biliary, iliac, femoral and popliteal as well as other peripheral vasculatures.

As used herein with respect to an implantable medical device, "device body" refers to an implantable medical device in a fully formed utilitarian state with an outer surface to which no layer of material different from that of which the device is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

Implantable medical devices can be made of virtually any material including metals and/or polymers. Devices made from bioabsorbable and/or biostable polymers could also be used with the embodiments of the present invention. The device can be, for example, a bioabsorbable stent. The material from which the device is manufactured is not a limitation with respect to the present invention.

As used herein, a "balloon" refers to the well-known in the art device, usually associated with a vascular catheter, that comprises a relatively thin, flexible or elastomeric material that when positioned at a particular location in a patient's vessel can be expanded or inflated to an outside diameter that is essentially the same as the inside or luminal diameter of the vessel in which it is placed. Inflation of the balloon may be effected by any means known or as shall become known in the art. With respect to the present invention, the particular design of the balloon is not significant, and a wide variety of designs may be used.

In general, the coating may be applied to a surface of the substrate, which may be the outer surface of a device body for an implantable medical device, or the outer surface of a catheter balloon, that is the surface in contact with bodily fluids or tissues. For other devices the outer surface, or other appropriate surface, may be coated. For a stent the outer surface includes the luminal, sidewall, and abluminal surfaces.

How to Make

The typical manufacturing process for coating a stent (example of a substrate) is dissolving or dispersing a polymer, optionally with other additives, and a drug, in a solvent (a fluid), and disposing the resulting coating solution over the stent by procedures such as spraying or immersing the stent in the solution. Such coating procedures are well-known in the art.

In some aspects of the present invention, application of the coating solution to the stent is accomplished by spraying a solution onto the stent, the solution being atomized with a compressed gas (non-limiting examples of compressed gases include, air, nitrogen, argon, or another inert gas, or a supercritical fluid may be used). Important aspects of the spray coating process include the pressure of the atomizing gas and the spray nozzle to part distance. Multiple passes under the sprayer and dryer may be required to obtain a coating layer.

After the solution has been disposed over the stent, the solvent is removed, or substantially removed, by evaporation. When the solvent is removed, what is left is the solid layer comprising the substances dissolved in the coating solution. The process of solvent removal can be accelerated by using an elevated temperature, and/or using a flow of a gas or supercritical fluid over or past the stent. The layer remaining after solvent has been substantially removed may include a small amount of residual solvent as removal of absolutely all of the solvent may be very difficult.

Multiple spraying and drying operations may be required to form a coating layer.

Embodiments of the present invention encompass coatings in which the coating layer, or materials included in the coating layer such as a polymer and/or drugs, are not covalently bound or chemically bound to the surface to which the coating is applied (the substrate surface, or a previously applied coating layer).

Method of Treating or Preventing Disorders

Embodiments of the present invention encompass methods of treating a patient (animal, including a human) with a coated medical device wherein the coating may be any one of the embodiments, or any combination of embodiments of the present invention. In particular, an implantable device with a coating as described herein may be used to treat, prevent, mitigate, reduce, or diagnose various conditions or disorders, or to provide a pro-healing effect. Non-limiting examples of such conditions or disorders include: coronary artery disease, carotid artery disease, peripheral arterial disease, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction, benign pancreatic disease, and tumor obstruction tumors (in, for example, the esophagus, the trachea/bronchi, etc.).

In a preferred embodiment, the method of treatment encompasses treatment of a vascular disease or condition with a stent including zotarolimus and dexamethasone acetate, and in a more preferred embodiment, the zotarolimus and dexamethasone acetate are included in the same coating layer on the stent which also includes a fluoropolymer.

Other Drugs

Other drugs that may be suitable for use in the embodiments of the present invention, depending, of course, on the specific disease being treated, include, without limitation, anti-restenosis, pro- or anti-proliferative, anti-inflammatory, anti-neoplastic, antimitotic, anti-platelet, anticoagulant, anti-fibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

The term "anti-proliferative" as used herein, refers to a drug that works to block the proliferative phase of acute cellular rejection. The anti-proliferative drug can be a natural proteineous substance such as a cytotoxin or a synthetic molecule. Other drugs include, without limitation, anti-proliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, rapamycin (sirolimus) and its functional or structural derivatives and the functional or structural derivatives of everolimus (outlined above with olimus drugs), FKBP-12 mediated mTOR inhibitors, and pirfenidone. Additional examples of cytostatic or antiproliferative drugs include, without limitation, angiopeptin, and fibroblast growth factor (FGF) antagonists.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Alternatively, the anti-inflammatory drug can be a biological inhibitor of pro-inflammatory signaling molecules. Anti-inflammatory drugs may be bioactive substances including antibodies to such biological inflammatory signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other drugs include, without limitation, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), γ-hiridun, mometasone, imatinib mesylate, midostaurin, feno fibrate, and feno fibric acid.

Other drugs that have not been specifically listed may also be used. Some drugs may fall into more than one of the above mentioned categories. Prodrugs thereof, co-drugs thereof, and combinations thereof of the above listed drugs are also encompassed in the various embodiments of the present invention.

EXAMPLES

The examples presented in this section are provided by way of illustration of the current invention only and are not intended nor are they to be construed as limiting the scope of this invention in any manner whatsoever. Each of the examples the follows relates to the coating of 3 mm×12 mm VISION® (Abbott Cardiovascular Systems Inc.) stent, which has a coatable surface area of 0.557 $cm^2$, or to results from experiments using the coated stents.

Example 1

All stents were cleaned by sonication in isopropyl alcohol followed by treatment with an argon gas plasma to prepare the surface. By spraying, a primer coating of 2% (w/w) poly(n-butyl methacrylate) (PBMA) was applied from acetone/cyclohexanone (70/30) (w/w) in a series of passes. After baking at 80° C. for 30 minutes, this resulted in about 50 μg of PBMA deposited on the stent. A drug reservoir formulation was made in acetone/cyclohexanone (70/30) (w/w) with 2% (w/w) PVDF-HFP, and a weight ratio of everolimus (Novartis) to dexamethasone (Sigma, USP), of 1:2 with a total drug/polymer ratio (w/w) of 1:4. This solution was applied to the stent in by a series of spray-dry passes to obtain the target weight of drug reservoir coating on the stent (a coating layer may require multiple passes under the coater). The spraying operation was carried out with a custom made spray coater equipped with a spray nozzle, a drying nozzle, and a means to rotate and translate the stent under the nozzles using the processing parameters outlined in Table 1. Subsequent to coating, all stents were baked in a forced air convection oven at 50° C. for 60 minutes. After baking the coating, the stents were crimped onto 3.0×12 mm VISION catheters, placed in protective tubular coils, and then sealed in TYVEK™ pouches. The stents were sterilized by ethylene oxide sterilization using a cycle with 60-90 minutes of steam conditioning at 95-125° F. followed by ETO injection with three hours of dwell time. After ETO sterilization, the TYVEK™ pouches were over wrapped in foil pouches and heat sealed under argon.

TABLE 1

Spray Processing Parameters Drug Reservoir Coating

| Spray Head | |
|---|---|
| Spray nozzle to stent distance (mm) | 11 |
| Solution flow rate (ml/min) | 0.06 |
| Atomization pressure (psi) | 10 |
| Dry Heat Nozzle | |
| Drying nozzle temp (° C.) | Ambient |
| Drying nozzle pressure (psi) | 20 |
| Spray nozzle to stent distance (mm) | 11 |
| Flow Rate and Coating Weight | |
| Target Flow Rate in µg/pass | 20 |
| Target Weight (µg) | 960 |

Figure 1B:
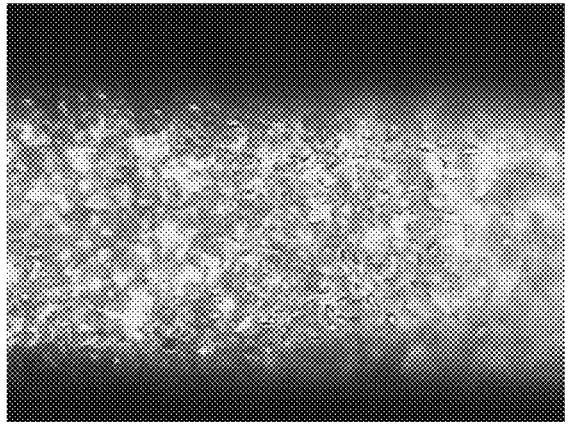

The total drug to polymer mass ratio was 1:4 and the mass ratio of everolimus to dexamethasone was 1:2 with a target dose for everolimus and dexamethasone of 100 and 200 µg/cm$^2$, respectively. FIGS. 1A and 1B are optical micrographs taken in reflectance mode with crossed polarizers at magnifications of 200× and 500×, respectively, of a coated stent after sterilization. As seen in FIGS. 1A and 1B the crystallization is significant.

Example 2

Figure 2A:
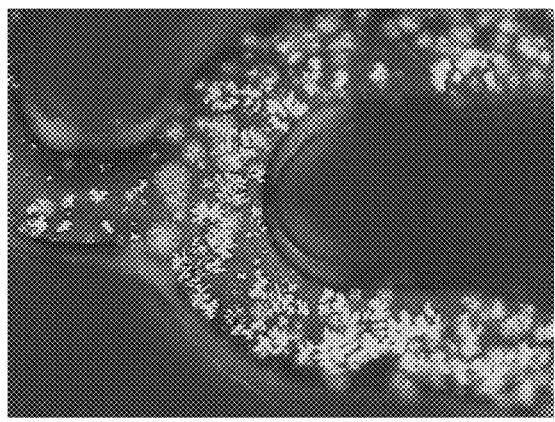
FIGS. 2A and 2B depict a coated stent before sterilization at magnifications of 200 and 500, respectively.
Figure 2B:
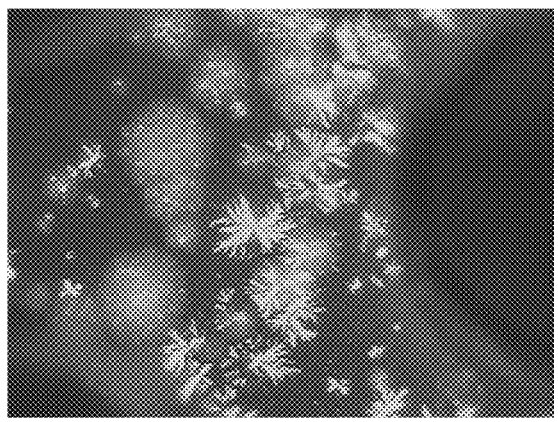
Figure 2C:
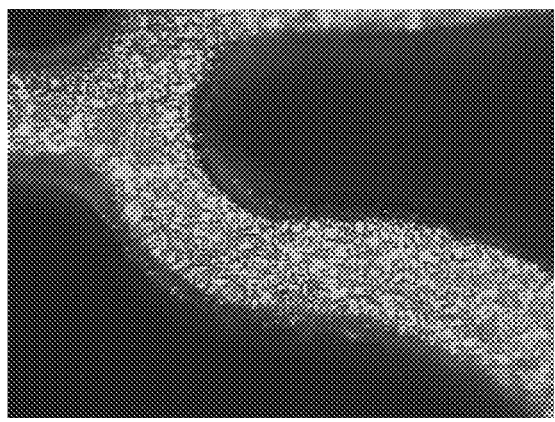
FIGS. 2C and 2D depict a coated stent after sterilization at magnifications of 200 and 500, respectively.
Figure 2D:
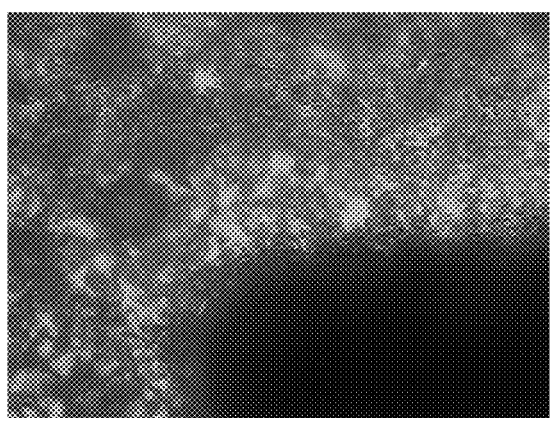

Dual drug coated stents were prepared as described in Example 1. Stents were sterilized with ethylene oxide. The total drug to polymer mass ratio was 1:4 and the mass ratio of everolimus to dexamethasone was 1:2 with a target dose for everolimus and dexamethasone of 100 and 200 µg/cm$^2$, respectively. FIGS. 2A and 2B are magnifications of 200× and 500×, respectively, of a coated stent before sterilization. FIGS. 2C and 2D are taken at magnifications of 200× and 500×, respectively, of a coated stent after sterilization. As seen in FIGS. 2A-2D, the crystallization of dexamethasone is significant, and increases after ethylene oxide sterilization.

Example 3

Figure 3A:
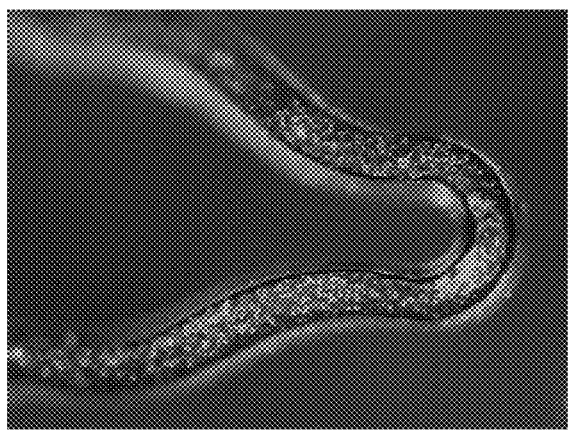
FIGS. 3A and 3B depict a coated stent before sterilization at magnifications of 100 and 200, respectively.
Figure 3B:
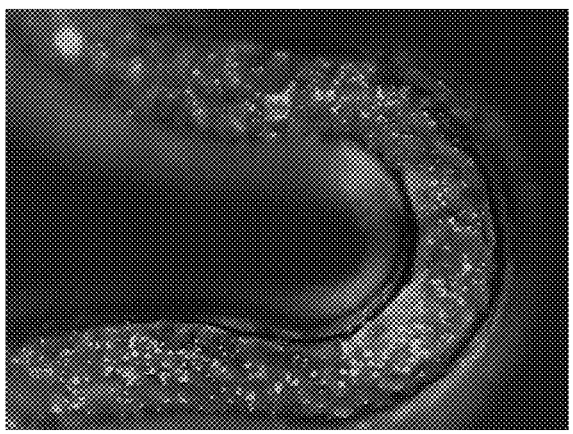
Figure 3C:
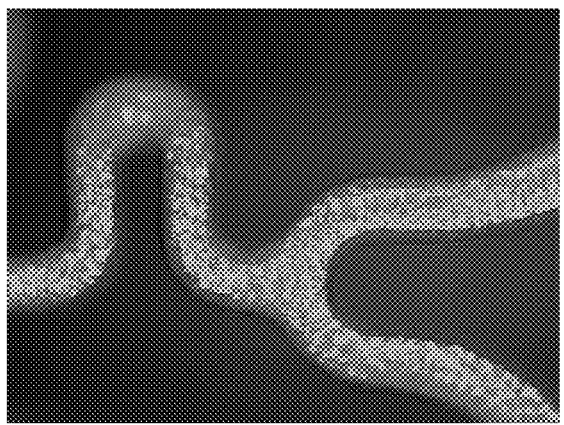
FIGS. 3C and 3D depict a coated stent after sterilization at magnifications of 100 and 200, respectively.
Figure 3D:
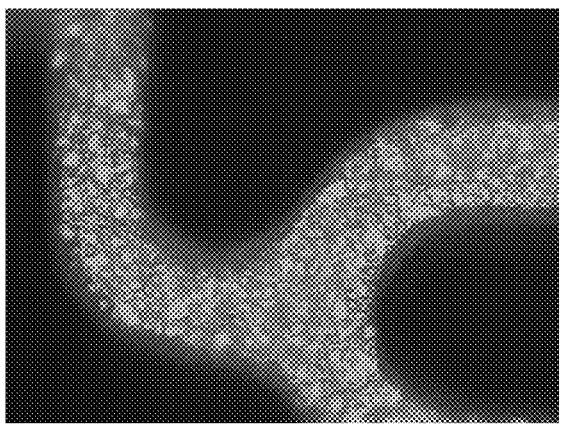

Stents were cleaned, coated with primer, and then coated with a drug-polymer layer as described in Example 1 except that the solvent utilized for the application of the coating layer was 100% acetone. Stents were sterilized with ethylene oxide. The total drug to polymer mass ratio was 1:4 and the mass ratio of everolimus to dexamethasone was 1:2. FIGS. 3A and 3B were taken at magnifications of 100× and 200×, respectively, of a coated stent before sterilization. FIGS. 3C and 3D are magnifications of 100 and 200, respectively, of a coated stent after sterilization. As seen in FIGS. 3A-3D, the crystallization of dexamethasone is significant, and increases after ethylene oxide sterilization.

Figure 4:
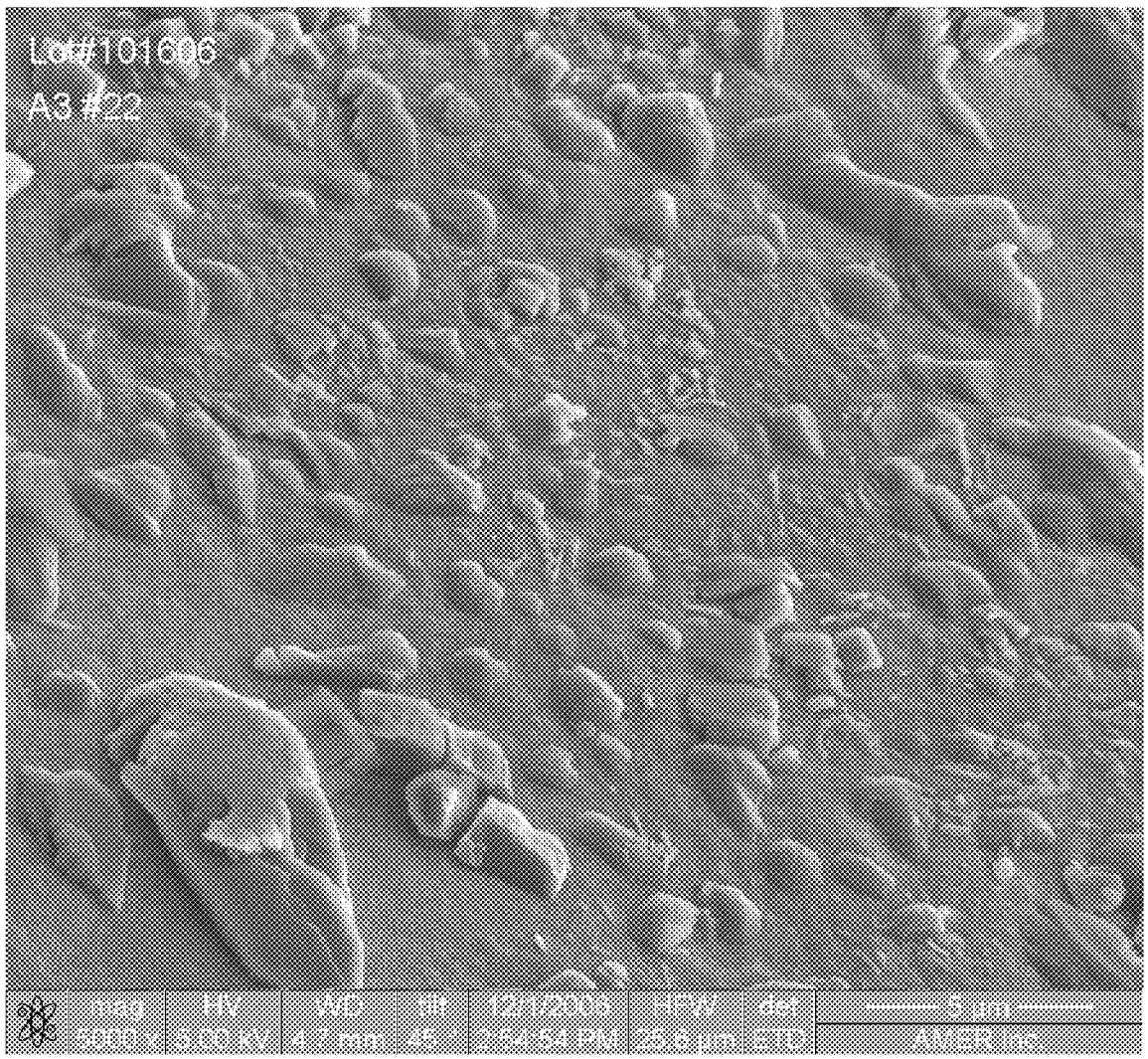
FIG. 4 depicts an SEM of the surface of a coated stent.

FIG. 4 is a SEM micrograph of the surface of a stent from Example 1 taken at 5000× magnification. As seen in FIG. 4, the dexamethasone crystals form at the surface of the coating as well as in the bulk.

Example 4

Figure 5A:
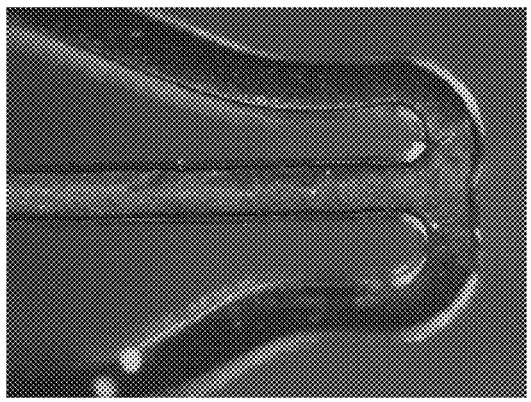
FIGS. 5A and 5B depict two different coated stents after sterilization at a magnification of 100.
Figure 5B:
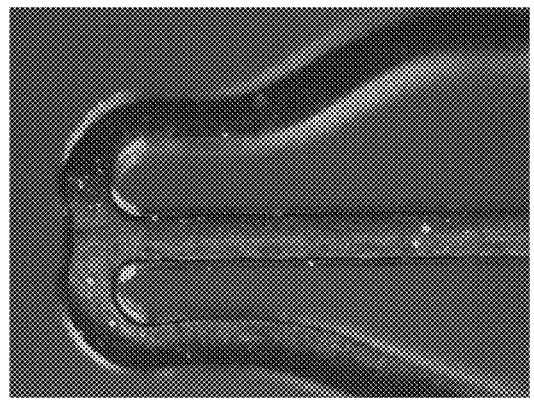

Stents were coated with a coating layer including dexamethasone acetate instead of dexamethasone. Stents were cleaned, coated with primer, and then coated with a drug-polymer layer as described in Example 1, using for the application of the coating layer, a solvent blend of acetone/cyclohexanone 70/30 (w/w). Stents were sterilized with ethylene oxide. The total drug to polymer mass ratio was 1:4 and the mass ratio of everolimus to dexamethasone acetate was 1:2, with a target dose for everolimus and dexamethasone acetate of 100 and 200 µg/cm$^2$, respectively. FIGS. 5A and 5B are optical micrographs under crossed polarizers taken at 100× magnification of two different coated stents after ETO sterilization. As seen in FIGS. 5A and 5B, the number of drug crystals is significantly reduced.

Example 5

Figure 6A:
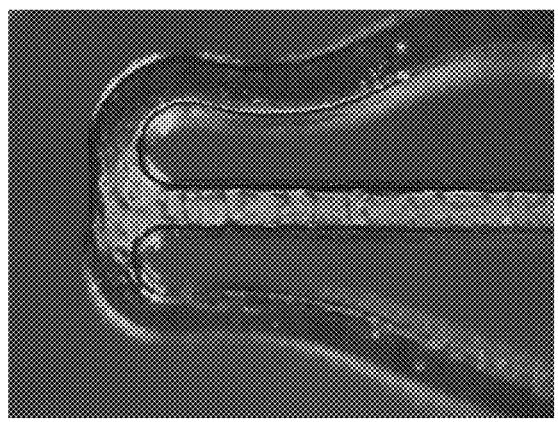
FIGS. 6A and 6B depict two different coated stents after sterilization at a magnification of 100.
Figure 6B:
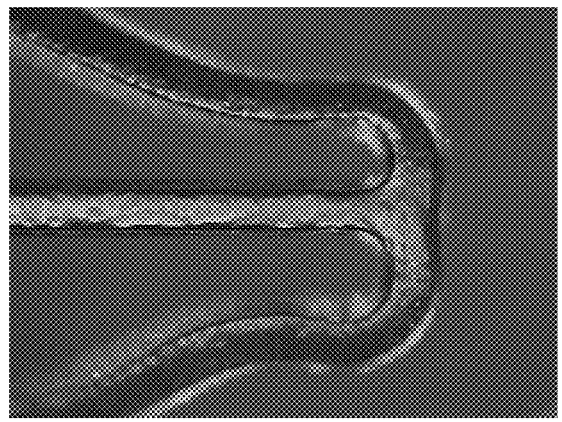

Stents were coated with a coating layer including dexamethasone acetate instead of dexamethasone, and zotarolimus instead of everolimus. Stents were cleaned, coated with primer, and then coated with a drug-polymer layer as described in Example 1, using for the application of the coating layer a solvent system of 100% acetone. The total drug to polymer mass ratio was 1:4 and the mass ratio of zotarolimus to dexamethasone acetate was 1:2, with a target dose for zotarolimus and dexamethasone acetate of 100 and 200 µg/cm$^2$, respectively. FIGS. 6A and 6B are magnifications of 100 of two different coated stents after sterilization. As seen in FIGS. 6A and 6B, the number of drug crystals is significantly reduced.

Example 6

A number of stents were coated at various zotarolimus to dexamethasone acetate ratios, and drug to polymer ratios. Small VISION™ 12 mm stents were utilized. All stents were cleaned and then plasma treated. Stents were coated with a primer layer of approximately 51 µg of poly(butyl methacrylate) (PBMA) by spraying from a solution of 2% (w/w) polymer in 2-butanone. More than one pass under the coater was required to obtain the target weight of polymer on the stent. The spraying operation was carried out as described in Example 1 with the processing parameters outlined in Table 2. Subsequent to coating, all stents were baked in a forced air convection oven at 80° C. for 30 minutes.

TABLE 2

Spray Processing Parameters Primer Layer Coating

| Primer | |
|---|---|
| Spray Head | |
| Spray nozzle to stent distance (mm) | 11 ± 1 |
| Solution flow rate | ~4 ml/hr |
| Atomization pressure (psi) | 8 |
| Dry Heat Nozzle | |
| Drying nozzle temp (° C.) | ambient |
| Drying nozzle pressure (psi) | 20 |
| Flow Rate and Coating Weight | |
| Target Weight (µg) | 51 |

After removal from the oven and weighing, the stents were coated with a solution of polymer, PDVF-HFP and zotarolimus (Abbott Labs) and dexamethasone acetate (AK Scientific, USP grade). The drug doses and drug to polymer ratio varied by study arm, and the target ratios are summarized in Table 3. The spraying operation was carried out in the same manner as for the primer spraying operation with the parameters outlined in Table 4. More than one pass under the coater was required to obtain the target weight of polymer and drug on the stent After the drug layer coating, the stents were baked in a forced air convection oven at 50° C. for 60 minutes. All drug-coated units were inspected for surface defects and dexamethasone acetate crystallization post-oven bake by reflectance polarization microscopy. Some stents used in analytical assays such as total drug content and drug release rate were subjected to no further processing steps prior to being assayed.

TABLE 3

Target Drug and Polymer Compositions for Coatings

| Arm | Zotarolimus:Dexamethasone Acetate Dose (μg/cm$^2$) | Drug:Polymer Ratio (w/w) | Total Dose (μg/cm$^2$) | Targeted day(s) for 80% release |
|---|---|---|---|---|
| A1 | 35:70 | 1:3.58 | 105 | 28 |
| A2 | 35:70 | 1:2.71 | 105 | 7 |
| A3 | 35:140 | 1:3.55 | 175 | 28 |
| A4 | 35:140 | 1:2.88 | 175 | 7 |
| A5 | 100:200 | 1:2.96 | 300 | 28 |
| A6 | 20:40 | 1:2.30 | 60 | 1 |

TABLE 4

Spray Processing Parameters Drug Layer Coating Drug Layer

| Spray Head | |
|---|---|
| Spray nozzle to mandrel distance (mm) | 11 ± 1 |
| Solution flow rate (ml/hr) | 4.1-6.5 (arm dependent) |
| Atomization pressure (psi) | 6 |
| Air Dry Heat Nozzle | |
| Drying nozzle temp (° C.) | ambient |
| Drying nozzle pressure (psi) | 20 |
| Flow Rate and Coating Weight | |
| Target Weight (μg) | Dependent on dose |

After baking the coating, the stents were crimped onto 3.0×12 mm VISION catheters, placed in protective tubular coils, and then sealed in TYVEK™ pouches and sterilized with ethylene oxide ("ETO sterilized"). After units were sterilized with ethylene oxide, they were over wrapped in argon filled foil pouches. Some sterilized stents were used in animal studies and others used for analytical assays. The stents were coated and processed in two different batch processes (preclinical builds).

Cumulative release of both zotarolimus and dexamethasone acetate was determined using a United States Pharmacopeia type VII tester in porcine serum with sodium azide 0.1% (w/v) added as the dissolution media. The cumulative release expressed is one minus the fractional amount of drug remaining on the stent divided by the theoretical quantity of drug per stent. Before release rate testing, stents from each arm were analyzed for total drug content. Using the actual drug reservoir coating weight for each stent, the percent of the drug reservoir which is drug was calculated. The values from several stents were averaged. Multiplying this percent of the drug reservoir which is drug by the reservoir coating weight for a stent gives the theoretical gravimetric drug content. This theoretical gravimetric drug content was then calculated for each stent undergoing release rate testing based on the drug reservoir coating weight for that stent.

The analytical assay results are summarized in Table 5 and 6 for the total drug content and the cumulative release, respectively. As shown in Table 5, there is a modest decrease in the total drug content after sterilization with ethylene oxide.

TABLE 5

Analytical Assay for Total Drug Content

| | Non-sterile | | ETO Sterilized | |
|---|---|---|---|---|
| Arm | Zotarolimus | Dex Acetate[1] | Zotarolimus | Dex Acetate |
| A1 | 98.1% ± 5.0% | 95.7% ± 1.7% | 94.0% ± 0.4% | 94.9% ± 0.4% |
| A2 | 95.0% ± 0.2% | 98.4% ± 0.7% | 93.6% ± 0.8% | 97.1% ± 0.8% |
| A3 | 100.7% ± 2.5% | 95.9% ± 0.7% | 94.5% ± 1.1% | 96.5% ± 0.7% |
| A4 | 91.4% ± 1.3% | 96.7% ± 0.7% | 92.0% ± 0.9% | 98.0% ± 1.3% |
| A5 | 104.7% ± 0.6% | 96.8% ± 0.2% | 96.7% ± 0.6% | 98.4% ± 1.3% |
| A6 | 90.0% ± 1.4% | 96.3% ± 1.3% | 89.9% ± 1.0% | 95.3% ± 0.8% |

[1]Dexamethasone acetate

Table 6 below illustrates that for some stent coatings controlled release of both drugs was obtained.

TABLE 6

Cumulative Release Results for Non-Sterile Coated Stents
Measured in vitro in Porcine Serum

| | 1 day | | 3 days | | 7 days | |
|---|---|---|---|---|---|---|
| Arm | Zot[1] | Dex A[2] | Zot | Dex A | Zot | Dex A |
| A1 | 21.8% ± 0.4% | 34.0% ± 1.5% | 34.4% ± 2.5% | 52.9% ± 1.8% | 43.6% ± 3.0% | 64.0% ± 1.9% |
| A2 | 41.9% ± 4.6% | 65.6% ± 4.8% | 68.2% ± 7.7% | 91.0% ± 2.9% | 86.3% ± 4.8% | 97.9% ± 0.6% |
| A3 | 21.5% ± 3.0% | 29.1.% ± 1.8% | 25.1% ± 1.0% | 38.3% ± 0.5% | 33.0% ± 3.4% | 52.5% ± 5.6% |
| A4 | 30.1% ± 2.5% | 68.8% ± 2.1% | 50.1% ± 2.4% | 90.7% ± 1.2% | 72.2% ± 10.5% | 97.8% ± 0.6% |
| A5 | 21.3% ± 2.5% | 23.0% 1.7% | 27.2% ± 1.0% | 37.7% ± 0.9% | 43.0% ± 3.0% | 59.3% ± 3.6% |
| A6 | 78.6% ± 2.3% | 92.6% ± 0.8% | — | — | — | — |

[1]Zot = Zotarolimus
[2]Dex A = Dexamethasone Acetate

Figure 7:
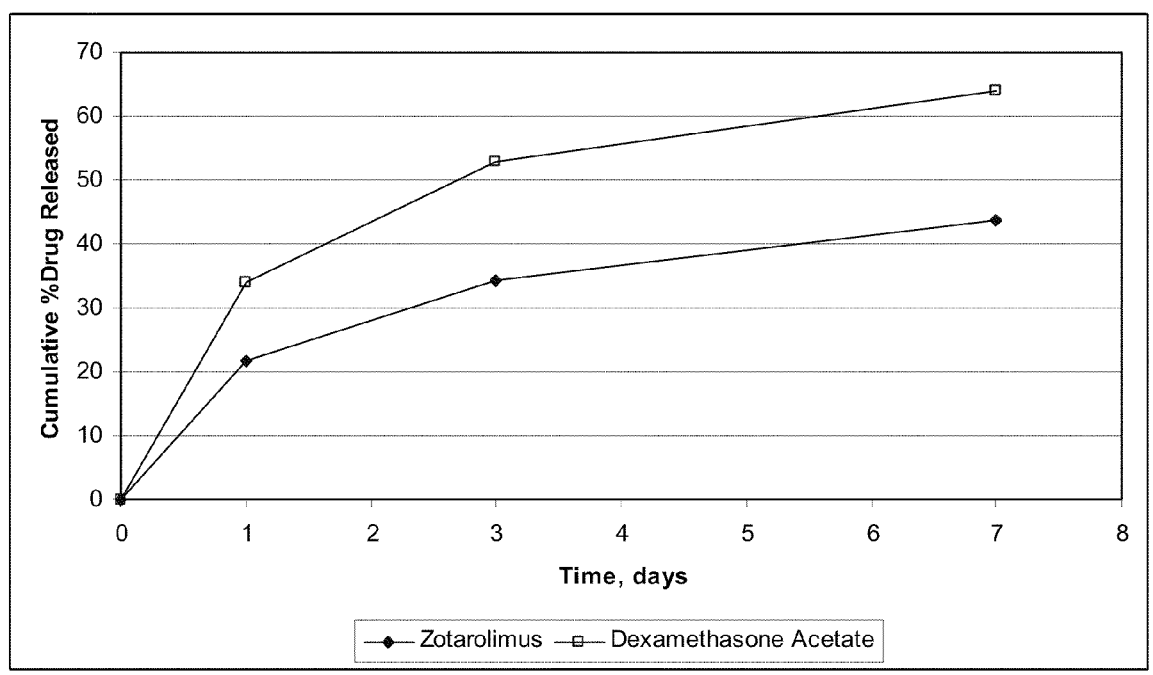
FIG. 7 depicts the cumulative release profile of an olimus drug and a dexamethasone derivative from a coated stent wherein the coating is an embodiment of the present invention.

FIG. 7 depicts the cumulative release profiles for both dexamethasone acetate and zotarolimus from the stent of Arm 1, with a total drug dose of 105 µg/cm$^2$, 35 µg/cm$^2$ of zotarolimus, and 70 µg/cm$^2$ of dexamethasone acetate.

Example 7

The stents coated in Example 6 were utilized in a preclinical porcine safety study. Six study arms utilized the stents outlined as arms 1-6 in Example 6. Arm 7 was the control, an everolimus-eluting VISION® coronary stent with a dose of 100 µg/cm$^2$ and a release rate of approximately 80% at 28 days. The study involved the implantation of the coated stents into domestic farm swine ("pigs") with three stents per animal, each of which was placed into a coronary artery. The duration of implantation was 28-days. After the 28 days, the animals were euthanized and histopathology assays were performed.

Figure 8:
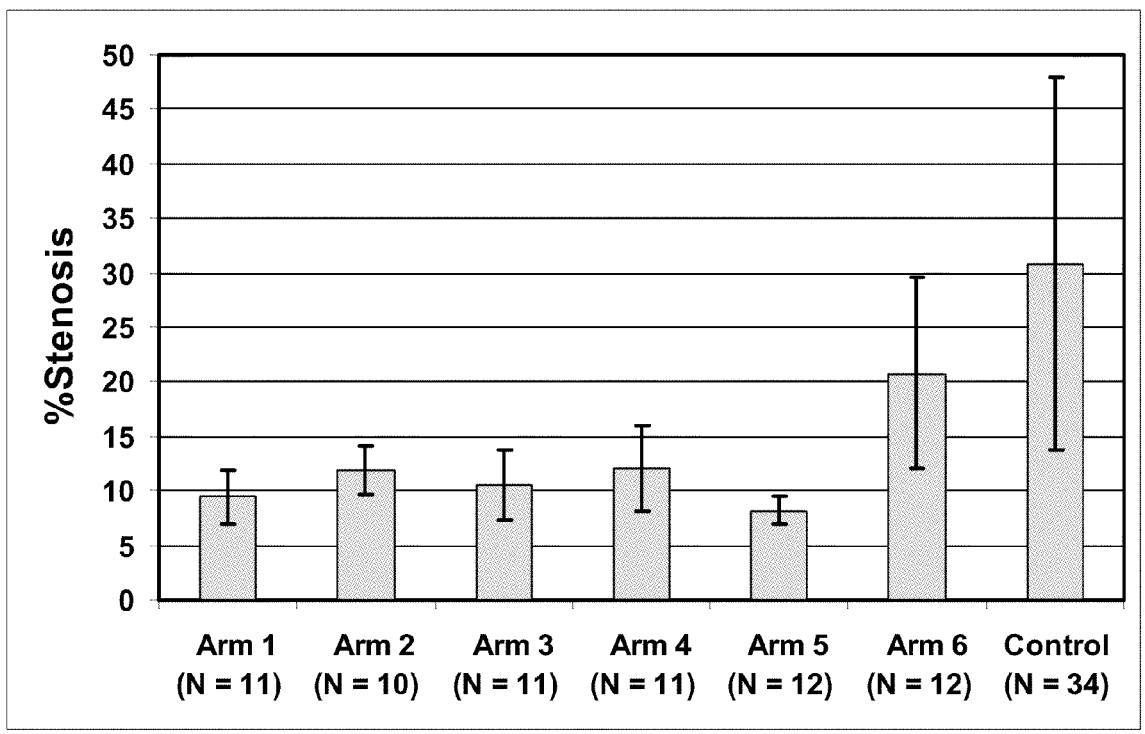
FIG. 8 depicts the % stenosis for different coated stents in a 28-day porcine pre-clinical study.

FIG. 8 illustrates the % stenosis for the seven arms of the study. The data presented here excludes processing artifacts. The data indicate that a statistical difference (p-value less than or equal to 0.05) exist for all arms compared to the control except for arm 6.

Figure 9:
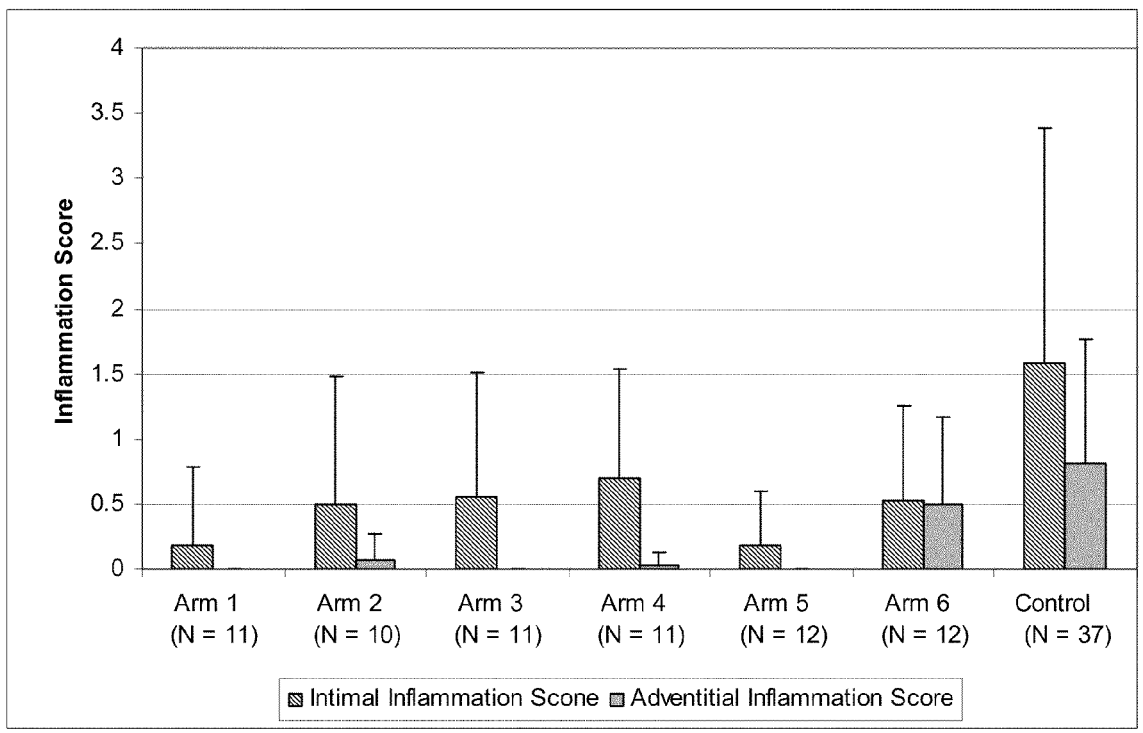
FIG. 9 depicts the inflammation for different coated stents in a 28-day porcine pre-clinical study.
Figure 10:
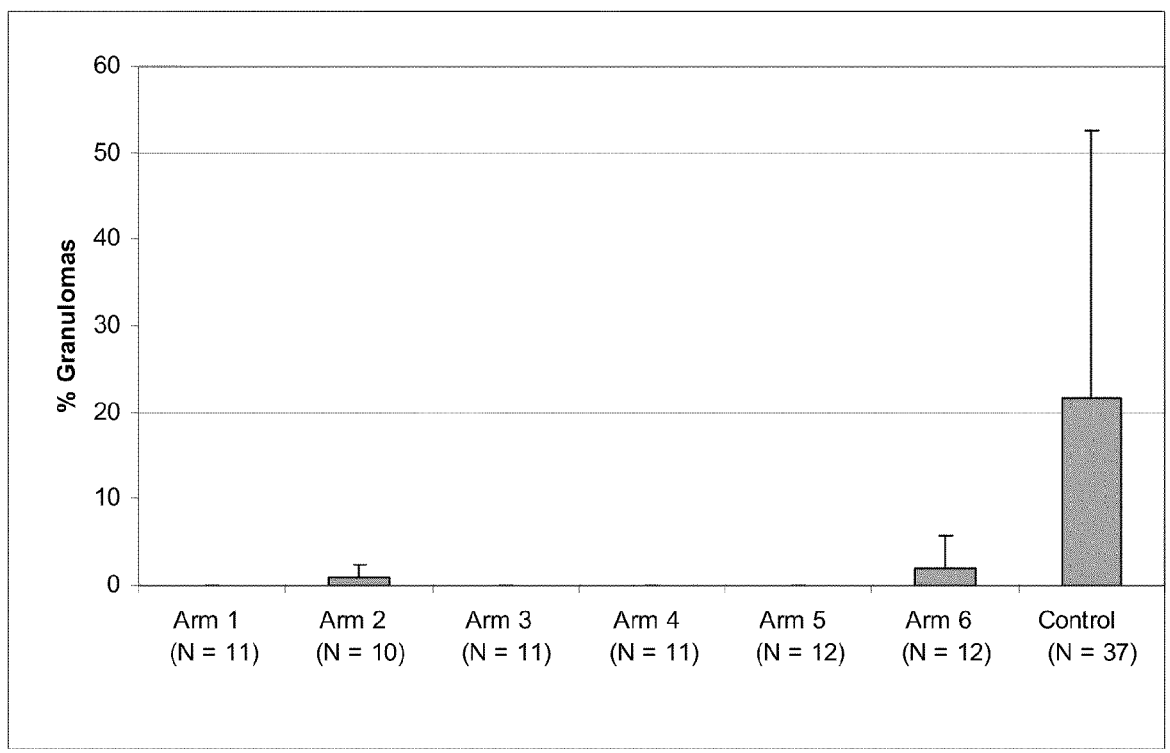
FIG. 10 depicts the % granulomas for different coated stents in a 28-day porcine pre-clinical study.

FIGS. 9 and 10 illustrate the inflammation scores and the % granulomas for the study arms. FIG. 9 includes all data except processing artifacts. If stents with severe granulomas are excluded, in addition to excluding the processing artifacts, the everolimus only control arm exhibits no statistical difference in inflammation score compared to the dual drug arms. For the data in FIG. 9, there is no statistical difference among the 7 arms for the Intimal Inflammation score. However, for the adventitial inflammation score, statistical significance was reached for Arms A1, A3 and A5 vs. the control arm (based upon a Wilcoxon/Kruskal-Wallis subgroup analysis using a p-value of 0.00833). As FIG. 10 illustrates, the percent granulomas are highest for the everolimus only control arm. These rates of granulomas do not necessarily translate to other animal species or to the clinical environment. Granulomas are much more common in pigs than in other animal species, such as rabbits. However, the effect of the inclusion of dexamethasone, an anti-inflammatory, is clearly illustrated as the highest rate of granulomas is for the control arm which does not include any anti-inflammatory drug.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

What is claimed is:

1. An implantable medical device comprising:
 a device body with an outer surface;
  a coating comprising
   one or more coating layers disposed over the surface wherein one coating layer comprises
    a PVDF-HFP polymer;
    an olimus drug selected from the group consisting of everolimus and zotarolimus;
    substantially amorphous dexamethasone acetate;
   wherein the mass ratio of everolimus or zotarolimus to dexamethasone acetate is from about 1:2 to about 1:4; and
   the drug to polymer ratio is from about 1:2.3 to about 1:4.

2. The device of claim 1, wherein the everolimus or zotarolimus dose is between about 10 and about 600 µg/cm$^2$ and the dose of dexamethasone acetate is between 10 and about 600 µg/cm$^2$.

3. The device of claim 1, wherein said olimus drug is everolimus.

4. The device of claim 1 wherein said olimus drug is zotarolimus.

5. The device of claim 1, wherein the implantable medical device is a stent.

6. The device of claim 1, wherein the implantable medical device is a catheter balloon.

7. The device of claim 2, wherein and the PVDF-HFP polymer comprises at least 25% vinylidene fluoride by weight.

8. The device of claim 1, wherein the PVDF-HFP polymer comprises at least 25% vinylidene fluoride by weight.

9. The device of claim 1, that exhibits negligible dexamethasone acetate crystallization.

10. The device of claim 1, wherein the cumulative drug release of the olimus drug at 24 hours is not more than 50% of the original total olimus drug content.

11. The device of claim 1, wherein the cumulative drug release of dexamethasone acetate at 24 hours is not more than 50% of the original total dexamethasone acetate content.

12. A method of treating a medical condition in a patient comprising, implanting in the patient in need thereof a device according to claim 1.

13. The method of claim 12, wherein the medical condition is selected from the group consisting of restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, and combinations of these.

14. The method of claim 12, wherein the implantable medical device is a catheter balloon.

15. The method of claim 14, wherein the implantable medical device is a stent.

16. The method of claim 15, wherein the cumulative drug release of the everolimus or zotarolimus is not more than 50% of the total everolimus or zotarolimus content at 24 hours.

17. The method of claim 15, wherein the cumulative drug release of the dexamethasone acetate is not more than 50% of the total dexamethasone acetate content at 24 hours.

* * * * *